United States Patent [19]  [11] Patent Number: 4,994,274
Chan et al. [45] Date of Patent: Feb. 19, 1991

[54] INTRAOCULAR PRESSURE REDUCING 11,15-DIACYL PROSTAGLANDINS AND METHOD OF USING

[75] Inventors: Ming F. Chan, Santa Ana; David F. Woodward, El Toro, both of Calif.

[73] Assignee: Allergan, Inc., Irvine, Calif.

[21] Appl. No.: 385,645

[22] Filed: Jul. 27, 1989

[51] Int. Cl.$^5$ .................. A61K 31/22; A61K 31/215; A61K 31/19

[52] U.S. Cl. ..................................... 424/427; 514/530

[58] Field of Search ........................ 514/530; 424/427

[56] References Cited

U.S. PATENT DOCUMENTS

| | | | |
|---|---|---|---|
| 3,853,854 | 12/1974 | Weinshenker et al. | 549/415 |
| 3,940,438 | 2/1976 | Weinshenker | 562/503 |
| 3,941,886 | 3/1976 | Weinshenker | 264/135 |
| 4,001,306 | 1/1977 | Morozowich et al. | 560/231 |
| 4,016,184 | 4/1977 | Morton, Jr. | 260/408 |
| 4,033,989 | 7/1977 | Bundy | 260/408 |
| 4,049,678 | 9/1977 | Peterson | 549/267 |
| 4,055,593 | 10/1977 | Weinshenker et al. | 562/503 |
| 4,060,540 | 11/1977 | Barnady et al. | 556/441 |
| 4,099,014 | 7/1978 | Peterson | 562/463 |
| 4,599,353 | 7/1986 | Bito | 514/530 |
| 4,822,819 | 4/1989 | DeSantis et al. | 514/530 |
| 4,824,857 | 4/1989 | Goh et al. | 514/398 |
| 4,883,819 | 11/1989 | Bito | 514/573 |

FOREIGN PATENT DOCUMENTS

| | | |
|---|---|---|
| 0286903 | 4/1987 | European Pat. Off. . |
| 8806448 | 9/1988 | PCT Int'l Appl. . |
| 8903384 | 4/1989 | PCT Int'l Appl. . |

OTHER PUBLICATIONS

Jenny, Erwin and Schaublin, Peter *Tetrahedron Letters* 26: 2235-2238 (1974).
Kondo, Kiyosi et al., *Tetrahedron Letters*, 41: 3927-3930 (1978).
Gandolfo, C. et al., *Farmaco. Ed. Sci.* 27: 1125-1129 (1972).
Andersen, Neils, *Prostaglandin* 6(5): 361-374 (1974).
*Chem., Biochem., Pharmacol. Act Prostanoids, INCL. Proc. Symp.*, Meeting Date 1978, pp. 185-193; ed. Roberts, Stanley N. and Scheinman, Theodore; Pergamon Press (1979).
Bito, *Arch. Ophthalmol.* 105, (1987).
Camras et al., *Invest. Ophthalmol. Vis. Sci.* 16, 1125 (1977).
Keun Kim, *Investigative Ophthalmology* 14, 36 (1975).
Nilsson et al., *Exp. Eye Res.* 48, 707 (1989).
Siebold et al., *Prodrug* 5, 3 (1989).
Starr, *Exp. Eye Res.* 11, 170-177 (1971).
Zajacz et al., *The Eye: Reproduction, Obstetrics and Gynecology* 4, 316 (1976).

*Primary Examiner*—Merrell C. Cashion, Jr.
*Assistant Examiner*—Demetra J. Mills
*Attorney, Agent, or Firm*—Knobbe, Martens, Olson & Bear

[57] ABSTRACT

Compounds and their use for lowering intraocular pressure are disclosed herein.

49 Claims, No Drawings

INTRAOCULAR PRESSURE REDUCING 11,15-DIACYL PROSTAGLANDINS AND METHOD OF USING

BACKGROUND OF THE INVENTION

The present invention relates to a composition of matter and a method for reducing or maintaining intraocular pressure. More particularly it relates to a method and composition for reducing or maintaining intraocular pressure involving the administration of a composition containing an 11,15-diacyl prostaglandin in an ophthalmically acceptable carrier.

The method and compositions of the present invention are particularly useful for the management of glaucoma, a disease of the eye characterized by increased intraocular pressure. On the basis of its etiology, glaucoma has been classified as primary or secondary. For example, primary glaucoma in adults, congenital glaucoma, may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular tension is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical β-adrenoceptor antagonists have traditionally been the drugs of choice for treating glaucoma.

Certain eicosanoids, specifically C-1 esters of certain prostaglandins, have been reported to possess ocular hypotensive activity. However, prostaglandin ocular hypotensives generally suffer from the disadvantage of inducing conjunctival hyperemia of varying severity and duration, smarting, and foreign body sensation, as well as presenting solubility problems in certain opthalmically advantageous carriers.

This invention relates to derivatives of the known prostaglandins formulated in a pharmaceutically acceptable vehicle, and ophthalmic use of those prostaglandins. The present invention has numerous advantages over the prior art, including increasing duration of action and reduction of the aforementioned undesirable side effects.

SUMMARY OF THE INVENTION

In accordance with one aspect of the present invention, there is provided a method of treating ocular hypertension which comprises applying to the eye an amount sufficient to treat ocular hypertension of an 11,15-diacyl prostaglandin represented by compound formula I.

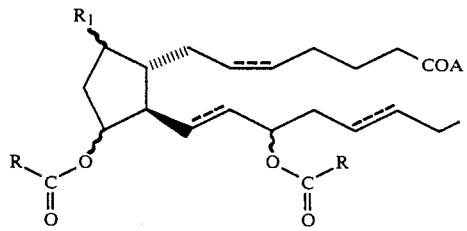

In formula I, the dashed bonds represent a double bond which can be in the cis or trans configuration, or a single bond; $R_1$ is $-OH$ or $=O$; A is $-OH$, or a pharmaceutically acceptable salt thereof or $-OR_1$ where $R_1$ is lower alkyl; the two R groups are independently an acyclic hydrocarbon, saturated or unsaturated, having from 1 to 20 carbon atoms, or $-(CH_2)_nR_2$ where n is 0–10 and $R_2$ is an aliphatic ring or an aromatic or heteroaromatic ring.

In accordance with another aspect of the present invention, there is provided an ophthalmically acceptable composition for reducing ocular hypertension which comprises at least one 11,15-diacyl prostaglandin described above, present in an ophthalmically acceptable excipient for topical application on the surface of the eye. Such an excipient is one which does not have a deleterious or untoward effect on the eye when used in normal treatment regimens.

Further features and advantages of the present invention will become apparent from the detailed description of preferred embodiments which follows, taken together with the examples and claims appended hereto.

DETAILED DESCRIPTION OF THE INVENTION

It has been discovered that certain prostaglandins lower intraocular pressure in man and other mammals when applied topically to the eye. Although the precise mechanism is not yet known, prostaglandins appear to increase aqueous humor outflow to restore a normotensive or hypotensive state. However, topical application of prostaglandins generally causes side effects such as conjunctival hyperemia, smarting and foreign body sensation which range in degree from undesirable to unacceptable, depending upon the particular patient and dosage necessary to produce a sufficient pressure regulating effect. In accordance with one aspect of the present invention, there has been provided a method for treating ocular hypertension which comprises administering to the eye a compound of formula I. It has further been discovered that these 11,15-diacyl $PGF_{2\alpha}$ derivatives are more effective than $PGF_{2\alpha}$ both in terms of degree and duration of activity. In addition, animals treated with formulations comprising these 11,15-diacyl compounds experience significantly reduced adverse side effects, notably ocular surface hyperemia.

In the foregoing illustration, as well as those provided hereinafter, wavy line attachments indicate either the alpha (α) or beta (β) configuration. The dotted lines on bonds between carbons 5 and 6 (C-5), between carbons 13 and 14 (C-13), and between carbons 17 and 18 (C-17) indicate a single or double bond which can be in the cis or trans configuration. If two solid lines are used at C-5, C-13, or C-17, it indicates a specific configuration for that double bond. Hatched lines used at position C-9, C-11 and C-15 indicate the α configuration. If one were to draw the β configuration, a solid triangular line would be used at either of these three positions.

The naturally occurring stereochemistry of $PGF_{2\alpha}$ includes the C-9, C-11 and C-15 position hydroxyl groups in the α configuration. In the compositions of the present invention, however, diacyl derivatives of prostaglandins having the C-9 or C-11 or C-15 hydroxyl group in the β configuration are also contemplated.

The 11,15-diacyl prostaglandins suitable for use in this invention can comprise any of a variety of acyl substituents at the 11 and 15 positions. As per formulas I, either R group can be an aliphatic acyclic hydrocarbon having from one to twenty carbon atoms, inclusive. Preferably each R group has from one to ten carbon atoms. Most preferably each R group is the same and is methyl, ethyl, propyl, butyl, pentyl, or an isomeric form thereof. The preferred isomeric forms are the iisobutyryl, isovaleryl, and pivaloyl isomers.

Alternatively each R group can comprise a cyclic component. In particular, either R group can be $(CH_2)_nR_2$ where n is 0–10 and $R_2$ is a saturated or unsaturated ring, preferably a saturated ring having from three to seven carbon atoms, inclusive, or an aromatic or heteroaromatic ring, preferably one having 5 to 7 carbon atoms, and having oxygen, nitrogen or sulfur in the case of a heteroaromatic ring. Preferably n is 0–4.

In all formulations provided herein broken line attachments to the cyclopentane ring indicate substituents in the α configuration. Thickened solid line attachments to the cyclopentane ring indicate substituents in the β configuration. For instance, 9β-PGF compounds have the same structure as the above $PGF_\alpha$ compounds, except that the hydroxyl at the C-9 position is in the β configuration. Also, the broken line attachment of the hydroxyl group to the C-15 carbon atom signifies the α configuration; therefore, compounds with the epi configuration for the hydroxyl group at C-15 are designated by using 15β and if there is no indication of the β configuration, the configuration is assumed to be α.

The preferred compounds of this invention are those which have the following structures.

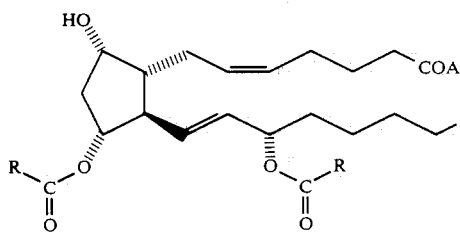

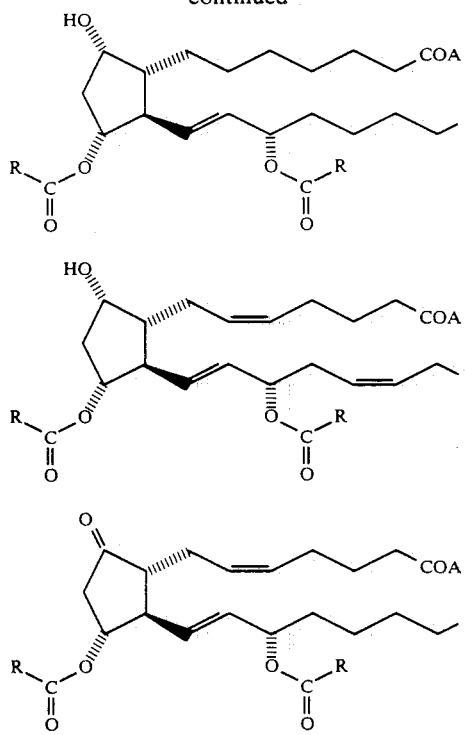

Within this preferred group, the most preferred compounds are those where both R groups are the same and are $-CH_3$, $-(CH_2)_3CH_3$, $-CH_2CH(CH_3)_2-CH(CH_3)_2$, $-CH_2C(CH_3)_3$ or $-C(CH_3)_3$.

Where A is —OH the acid can be converted to a salt $O^-X^+$ where $X^+$ is the cation component of any of a variety of pharmaceutically acceptable salts. A pharmaceutically acceptable salt may be prepared for any compound in this disclosure having a functionality capable of forming such salt, in particular, the carboxylic acid group at $C_1$ of the prostanoic acid analogs disclosed herein. A pharmaceutically acceptable salt is any salt which retains the activity of the parent compound and does not impart any deleterious or undesirable effect on the subject to whom it is administered and in the context in which it is administered.

A pharmaceutically acceptable salt of an acid may be derived from an organic or inorganic base. Such a salt may be a mono- or poly-valent ion. Of particular interest are the inorganic ions, sodium, potassium, calcium, magnesium and zinc. Organic ammonium salts may be made with amines, such as mono-, di-, and trialkyl amines or ethanolamines. Salts may also be formed with caffeine, tromethamine and similar molecules.

The optimal concentration of the prostaglandin derivative is a function of a variety of factors, such as desired frequency of application and duration of effect, level of adverse side effects and considerations implicated by the chemical nature of the carrier. In general, however, concentrations are contemplated within the range of from about 0.0001% to 1%, preferably from 0.001% to 0.1% by weight in relation to the pharmaceutically acceptable carrier.

The acylation reaction for producing the foregoing 11,15-diacyl compounds is illustrated in the Examples or is known to those skilled in the synthetic organic chemical arts.

The invention can be more fully understood by the following examples. All temperatures are in degrees centigrade.

EXAMPLE 1

Preparation of 11,15-Dipivaloyl $PGF_{2\alpha}$

Pivaloyl chloride (37 μl, 0.3 mmol) was added to a cold (0° C.) solution of $PGF_{2\alpha}$ methyl ester (38.8 mg, 0.105 mmol) in pyridine with stirring. The colorless mixture (some solid separated) was stirred at 0° C. for 20 minutes and then stored at 0° C. overnight (18 hours). The solvent and volatiles were evaporated in vacuo and the residue was partitioned between 10% citric acid and ethyl acetate. The aqueous layer was separated and extracted with ethyl acetate (3×7 ml). The combined organic layer was washed once with brine and dried over magnesium sulfate. Removal of solvent gave 60.7 mg of colorless oil which was chromatographed on silica gel (15-20% ethyl acetate in hexanes) to give 11,15-dipivaloyl $PGF_{2\alpha}$ methyl ester ($R_f$ 0.33 with 25% ethyl acetate in hexanes as eluent).

$^1$H NMR (300 MHz, CDCl$_3$): δ5.35-5.55 (4H, m), 5.19 (1H, br q, J=6 Hz), 4.75-4.81 (1H, m), 4.13-4.20 (1H, m), 3.68 (3H, s), 1.2-2.65 (20H, m), 1.17 and 1.18 (9H each, s) and 0.87 (3H, distorted t, J=6 Hz).

The product from the above experiment was stirred vigorously in a two phase mixture of 0.83M lithium hydroxide (0.2 ml, 0.166 mmol) and tetrahydrofuran (0.3 ml) at 25° C. for 22 hours. The mixture was cooled to 0° C., acidified with 10% citric acid and extracted with ethyl acetate (4×6 ml). The organic extract was washed with brine, dried over magnesium sulfate and concentrated in vacuo to give 45 mg crude product. Flash chromatography (silica gel, 30-40% ethyl acetate in hexanes) gave 11,15-dipivaloyl $PGF_{2\alpha}$ as a colorless oil, $R_f$ 0.43 with 40% ethyl acetate in hexanes.

$^1$H NMR (300 MHz, CDCl$_3$): δ5.3-5.6 (4H, m), 5.20 (1H, br q, J=6 Hz), 4.79 (1H, m), 4.18 (1H, t, J=5 Hz), 2.0-2.6 (12H, m), 2.3 (2H, t, J=7 Hz), 1.2-1.8 (6H, m), 1.18 (18H, 2×s) and 0.86 ppm (3H, distorted t, J=6 Hz).

$^{13}$C NMR (75 MHz, CDCl$_3$): δ178.6, 178.2, 132.5, 131.5 130.0, 128.9, 78.3, 73.6, 71.7, 50.7, 48.9, 40.5, 38.6, 38.4, 34.2, 33.0, 31.3, 26.9, 26.8, 26.2, 24.8, 24.5, 24.2 22.2 and 13.7 ppm.

IR (neat): 2500-3600, 2930, 2860, 1700, 1470, 1455, 1390, 1280, 1160, 1030 and 965 cm$^{-1}$.

MS (Cl, NH$_3$): m/z 540 (M+NH$_4$, 6.3%), 438 (19), 421 (10) 336 (13), 319 (100), 301 (55), 275 (8) and 191 (6).

HRMS: calcd for C$_{30}$H$_{54}$O$_7$N: 540.3908; found: 540.3900.

In a similar manner, the 11,15-diisobutyryl, the 11,15-diisovaleryl, and the 11,15-di-(t-butylacetyl) $PGF_{2\alpha}$ compounds were prepared.

11,15-diisobutyryl $PGF_{2\alpha}$ $^1$H NMR (300 MHz, CDCl$_3$): δ5.3-5.6 (4H, m), 5.22 (1H, distorted q, J=6 Hz), 4.8-4.9 (1H, m), 4.17 (1H, t, J=4.5 Hz), 2.0-2.6 (8H, m), 1.2-1.8 (14H, m), 1.1-1.16 (12H, overlapping doublets) and 0.86 ppm (3H, distorted t, J=6 Hz).

$^{13}$C NMR (75 MHz, CDCl$_3$): δ178.0, 177.2, 177.0, 132.7, 131.4, 130.0, 128.9, 78.3, 73.8, 71.8, 50.9, 49.1, 40.7, 34.3, 34.1, 33.8, 32.8, 31.3, 26.2, 24.8, 24.6, 22.3, 18.8, 18.7, 18.6, 18.5 and 13.7 ppm.

EXAMPLE 2

Intraocular Pressure Reducing Effect in Rabbits

Experimental quantities of several 11,15-diacyl $PGF_{2\alpha}$ compounds were prepared in accordance with the procedure of Example 1 or 2. The resulting 11,15-diacyl $PGF_{2\alpha}$ compounds were added to a polysorbate carrier in amounts to produce a 0.01% and 0.1% solution of each ester. A group of 8 experimental rabbits was treated by administering approximately one drop of each solution to the surface of the eye, and intraocular pressure was measured by applanation pneumatonometry (Model 30 RT manufactured by Digilab) at the time of administration and at intervals of 2, 3, 4, 6, 8 and 10 hours thereafter. The following data were obtained:

TABLE 1

INTRAOCULAR PRESSURE DECREASES AT PREDETERMINED TIMES (HR) AFTER PROSTAGLANDIN ADMINISTRATION

| Compound | PG Dose % | Time (Hours) | | | | | |
|---|---|---|---|---|---|---|---|
| | | 2 | 3 | 4 | 6 | 8 | 10 |
| Reduction in IOP (mm Hg) | | | | | | | |
| $PGF_{2\alpha}$-1-isopropyl ester | 0.01% | — | — | 1.3 | 5.8[2] | 3.5[2] | 2.9[2] |
| | 0.1% | — | — | 3.2[1] | 9.7[2] | 10.1[2] | 10.0[2] |
| 11,15-diisobutyryl $PGF_{2\alpha}$ | 0.01% | 2.1 | 6.9[2] | 6.9[2] | 4.1[2] | — | — |
| | 0.1% | — | — | 3.2 | 12.9[2] | 12.2[2] | 10.7[1] |
| | 1.0% | — | — | — | 11.0[2] | 11.4[2] | 14.2[2] |
| 11,15-diisovaleryl $PGF_{2\alpha}$ | 0.01% | — | — | 2.6 | 5.4[2] | 3.6[2] | 3.1[2] |
| | 0.1% | — | — | 1.2 | 13.9[2] | 12.0[2] | 13.0[2] |
| 11,15-dipivaloyl $PGF_{2\alpha}$ | 0.01% | — | — | 1.8 | 6.1[2] | 6.9[2] | 5.0[2] |
| | 0.1% | — | — | — | 6.7[2] | 10.5[2] | 10.0[2] |
| Percent Animal Exhibiting Ocular Surface Hyperemia | | | | | | | |
| $PGF_{2\alpha}$-1-isopropyl ester | 0.01% | 100 | 100 | 100 | 100 | 100 | 100 |
| | 0.1% | 100 | 100 | 100 | 100 | 100 | 87.5 |
| 11,15-diisobutyryl $PGF_{2\alpha}$ | 0.01% | 12 | 0 | 0 | 0 | — | — |
| | 0.1% | 100 | — | 100 | 100 | 100 | 87.5 |
| | 1.0% | 100 | — | 100 | 100 | 100 | 67 |
| 11,15-diisovaleryl $PGF_{2\alpha}$ | 0.01% | 100 | — | 100 | 100 | 75 | 0 |
| | 0.1% | 37 | — | 67 | 67 | 0 | 0 |
| 11,15-diisopivaloyl $PGF_{2\alpha}$ | 0.01% | 100 | 100 | 100 | 100 | 37.5 | 62.5 |
| | 0.1% | 100 | 100 | 100 | 100 | 100 | 100 |

1 - p < 0.05; 2 - p < 0.01.

Although this invention has been described in terms of certain preferred embodiments, these embodiments are meant to illustrate the invention, not limit it. Other embodiments that are apparent to those of ordinary skill in the art are also within the scope of this invention.

Accordingly, the scope of the invention is intended to be defined only be reference to the appended claims.

What is claimed:

1. A method of treating ocular hypertension which comprises applying to the eye in an ophthalmically acceptable excipient an amount sufficient to treat ocular hypertension of the compound:

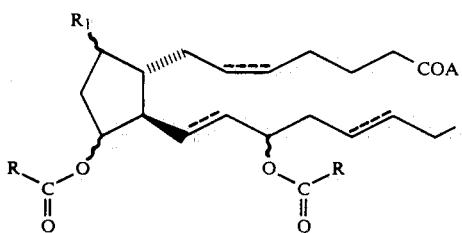

where dashed bonds represent a double bond which can be in the cis or trans configuration, or a single bond; $R_1$ is —OH or =O; A is —OH, or a pharmaceutically acceptable salt thereof or —$OR_1$ where $R_1$ is lower alkyl; the two R groups are independently an acyclic hydrocarbon, saturated or unsaturated, having from 1 to 20 carbon atoms, or —$(CH_2)_nR_2$ where n is 0–10 and $R_2$ is an aliphatic ring or an aromatic ring.

2. The method of claim 1 wherein $R_1$ is —OH.

3. The method of claim 2 wherein both R groups are the same and are methyl, ethyl, propyl, butyl, pentyl, or an isomeric form thereof.

4. The method of claim 3 where the C-5 and C-13 bonds are cis and trans double bonds respectively and the C-17 bond is a single bond, the compound having the following formula.

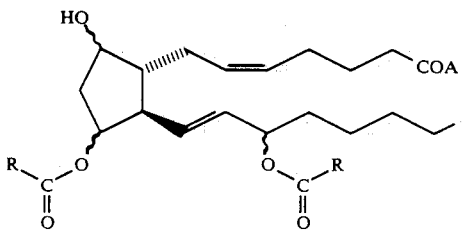

5. The method of claim 4 where the —OH group at C-9 and the C-11 and C-15 substituents are in the α configuration.

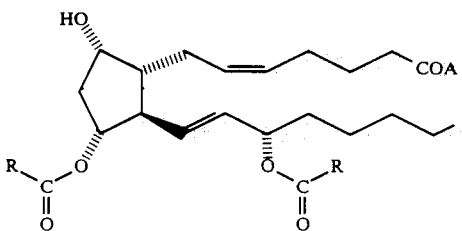

6. The method of claim 5 where both R groups are —$CH_3$, the diacetyl compound.

7. The method of claim 5 where both R groups are —$CH(CH_3)_2$, the diisobutyryl compound.

8. The method of claim 5 where the R groups are —$CH_2CH(CH_3)_2$, the di-isovaleryl compound.

9. The method of claim 5 where the R groups are —$C(CH_3)_3$, the dipivaloyl compound.

10. The method of claim 5 where the R groups are —$CH_2C(CH_3)_3$, the di-(t-butylacetyl) compound.

11. The method of claim 1 wherein $R_1$ is =O, the C-5 and C-13 bonds are respectively cis and trans double bonds and the C-17 bond is a single bond, and the C-11 and C-15 substituents are in the α configuration, the compound having the following formula.

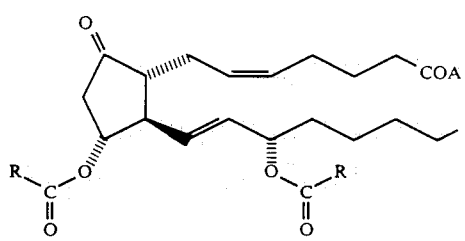

12. The method of claim 11 where both R groups are the same and are methyl, ethyl, propyl, butyl, pentyl, or an isomeric form thereof.

13. The method of claim 1 where the C-5 and C-17 bonds are single bonds, the C-13 bond is a trans double bond, and the C-11 and C-15 substituents are in the α configuration, the compound of the following formula.

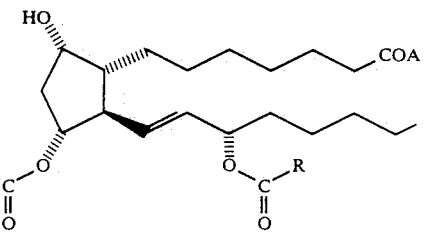

14. The method of claim 13 where both R groups are the same and are methyl, ethyl, propyl, butyl, pentyl, or an isomeric form thereof.

15. The method of claim 1 where the C-5 and C-17 bonds are cis double bonds, the C-13 bond is a trans double bond, and the C-9, C-11 and C-15 substituents are in the α configuration, the compound of the following formula.

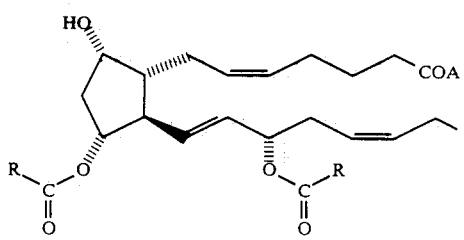

16. The method of claim 15 where both R groups are the same and are methyl, ethyl, propyl, butyl, or pentyl, or an isomeric form thereof.

17. An ophthalmically acceptable composition for reducing ocular hypertension which comprises at least one compound of the formula:

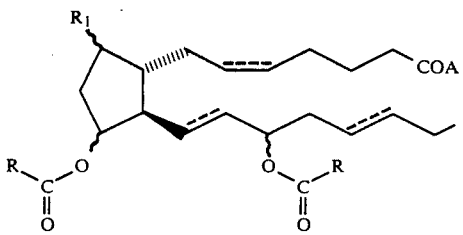

where dashed bonds represent a double bond which can be in the cis or trans configuration, or a single bond; $R_1$ is —OH or =O; A is —OH, or a pharmaceutically acceptable salt thereof or —$OR_1$ where $R_1$ is lower alkyl; the two R groups are independently an acyclic hydrocarbon, saturated or unsaturated, having from 1 to 20 carbon atoms, or —$(CH_2)_nR_2$ where n is 0–10 and $R_2$ is an aliphatic ring, an aromatic or a heteroaromatic ring.

18. A compound of the formula:

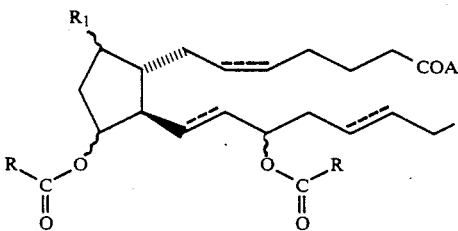

where dashed bonds represent a double bond which can be in the cis or trans configuration, or a single bond; $R_1$ is —OH or =O; A is —OH, or a pharmaceutically acceptable salt thereof or —$OR_1$ where $R_1$ is lower alkyl; the two R groups are independently an acyclic hydrocarbon, saturated or unsaturated, having from 1 to 20 carbon atoms, or —$(CH_2)_nR_2$ where n is 0–10 and $R_2$ is an aliphatic ring of from 3 to 7 carbon atoms or an aromatic ring.

19. The compound of claim 18 wherein $R_1$ is —OH.

20. The compound of claim 19 wherein both R groups are the same and are methyl, ethyl, propyl, butyl, pentyl, or an isomeric form thereof.

21. The compound of claim 20 where the C-5 and C-13 bonds are cis and trans double bonds respectively and the C-17 bond is a single bond, the compound having the following formula.

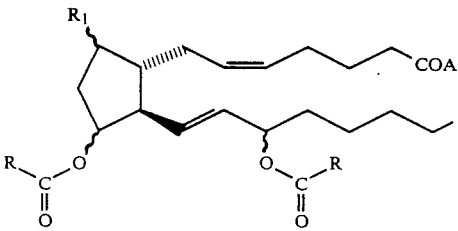

22. The compound of claim 21 where the C-9, C-11 and C-15 substituents are in the α configuration, the compound of the following formula.

23. The compound of claim 22 where both R groups are —$CH_3$, the diacetyl compound.

24. The compound of claim 22 where both R groups are —$CH(CH_3)_2$, the diisobutyryl compound.

25. The compound of claim 22 where the R groups are —$CH_2CH(CH_3)_2$, the diisovaleryl compound.

26. The compound of claim 22 where the R groups are —$C(CH_3)_3$, the di-pivaloyl compound.

27. The compound of claim 22 where the R groups are —$CH_2C(CH_3)_3$, the di(t-butylacetyl) compound.

28. The compound of claim 18 wherein $R_1$ is =O, the C-5 and C-13 bonds are respectively cis and trans double bonds, the C-17 bond is a single bond, and the C-9, C-11 and C-15 substituents are in the α configuration, the compound having the following formula.

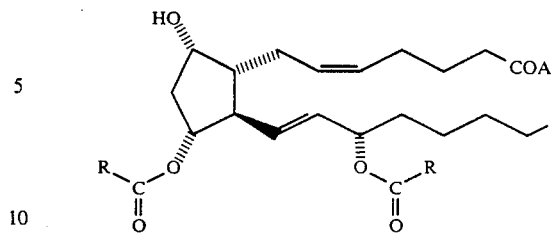

29. The compound of claim 28 where both R groups are the same and are methyl, ethyl, butyl, pentyl, or an isomeric form thereof.

30. The compound of claim 18 where the C-5 and C-17 bonds are single bonds, the C-13 bond is a trans double bond, and the C-9, C-11 and C-15 substituents are in the α configuration, the compound of the following formula.

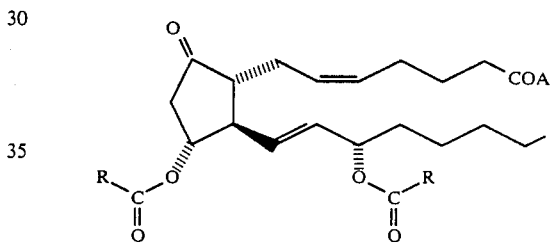

31. The compound of claim 30 where both R groups are methyl, ethyl, propyl, butyl, pentyl, or an isomeric form thereof.

32. The compound of claim 18 where the C-5 bond is a cis double bond, the C-13 bond is a trans double bond and C-17 is a cis double bond and the C-9, C-11 and C-15 substituents are in the α configuration, the compound of the following formula.

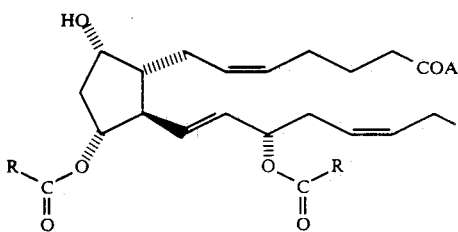

33. The compound of claim 32 where both R groups are the same and are methyl, ethyl, propyl, butyl, or pentyl, or an isomeric form thereof.

34. The compound of claim 33 where both R groups are —CH$_3$, —(CH$_2$)$_3$CH$_3$, —CH$_2$CH(CH$_3$)$_2$, CH$_2$C(CH$_3$)$_3$ or —C(CH$_3$)$_3$.

35. The composition of claim 17 wherein R$_1$ is —OH.

36. The composition of claim 35 wherein both R groups are the same and are methyl, ethyl, propyl, butyl, pentyl, or an isomeric form thereof.

37. The composition of claim 36 where the C-5 and C-13 bonds are cis and trans double bonds respectively and the C-17 bond is a single bond, the compound having the following formula.

38. The composition of claim 37 where the —OH group at C-9 and the C-11 and C-15 substituents are in the α configuration, the compound having the following formula.

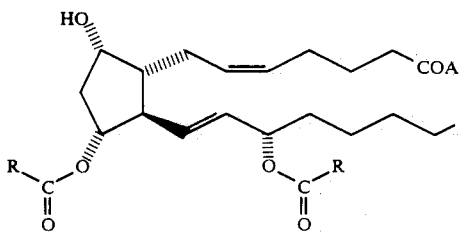

39. The composition of claim 38 where both R groups are —CH$_3$, the diacetyl compound.

40. The composition of claim 38 where both R groups are —CH(CH$_3$)$_2$, the diisobutyryl compound.

41. The composition of claim 38 where both R groups are —CH$_2$CH(CH$_3$)$_2$, the diisovaleryl compound.

42. The composition of claim 38 where both R groups are —C(CH$_3$)$_3$, the dipivaloyl compound.

43. The composition of claim 38 where both R groups are —CH$_2$C(CH$_3$)$_3$, the di-(t-butylacetyl) compound.

44. The composition of claim 17 wherein R$_1$ is =O, the C-5 and C-13 bonds are respectively cis and trans double bonds and the C-17 bond is a single bond, and the C-11 and C-15 substituents are in the α configuration, the compound having the following formula.

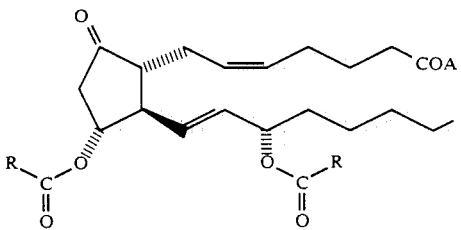

45. The composition of claim 44 where both R groups are the same and are methyl, ethyl, propyl, butyl, pentyl, or an isomeric form thereof.

46. The composition of claim 17 where the C-5 and C-17 bonds are single bonds, the C-13 bond is a trans double bond, and the C-11 and C-15 substituents are in the α configuration, the compound having the following formula.

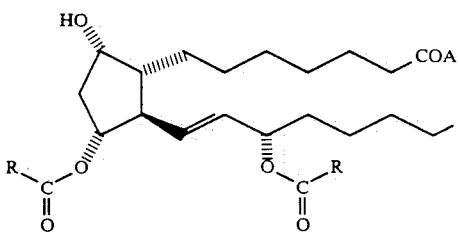

47. The composition of claim 46 where both R groups are the same and are methyl, ethyl, propyl, butyl, pentyl, or an isomeric form thereof.

48. The composition of claim 17 where the C-5 and C-17 bonds are cis double bonds, the C-13 bond is a trans double bond, and the C-9, C-11 and C-15 substituents are in the α configuration, the compound having the following formula.

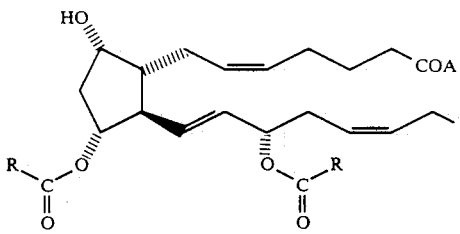

49. The composition of claim 48 where both R groups are the same and are methyl, ethyl, propyl, butyl, or pentyl, or an isomeric form thereof.

* * * * *